United States Patent [19]

Neinhaus et al.

[11] Patent Number: 4,853,368
[45] Date of Patent: Aug. 1, 1989

[54] METHYLCYCLODODECATRI-2,5,9-EN-1-OLS, A PROCESS FOR THEIR PREPARATION, AND THEIR USE

[75] Inventors: Jürgen Neinhaus; Rudolf Hopp, both of Holzminden; Wilhelm Göttsch; Egon Oelkers, both of Bevern, all of Fed. Rep. of Germany

[73] Assignee: Haarmann & Reimer GmbH, Holzminden, Fed. Rep. of Germany

[21] Appl. No.: 171,632

[22] Filed: Mar. 22, 1988

[30] Foreign Application Priority Data

Apr. 2, 1987 [DE] Fed. Rep. of Germany ....... 3711157

[51] Int. Cl.$^4$ ...................... A61K 7/46; C07C 35/205
[52] U.S. Cl. .......................................... 512/25; 512/8; 568/821
[58] Field of Search ........................ 568/821; 512/8, 25

[56] References Cited

U.S. PATENT DOCUMENTS

| | | | |
|---|---|---|---|
| 2,769,017 | 10/1956 | Reppe et al. | 568/821 |
| 2,978,464 | 4/1961 | Wiese et al. | 568/821 |
| 2,997,483 | 8/1961 | Gray | 568/821 |
| 3,089,904 | 5/1963 | Lippincott et al. | 568/821 |
| 3,333,010 | 7/1967 | Urbanek et al. | 568/821 |
| 3,723,478 | 3/1973 | Ohloff et al. | 568/821 |
| 3,816,349 | 6/1974 | Hall | 512/8 |
| 3,845,078 | 10/1974 | Lemberg | 568/821 |
| 3,896,180 | 7/1975 | Lemberg | 568/821 |
| 4,215,006 | 7/1980 | Mookherjee et al. | 512/8 |
| 4,359,588 | 11/1982 | Burzin et al. | 512/8 |
| 4,393,245 | 7/1983 | Hoffman et al. | 512/8 |
| 4,460,498 | 7/1984 | Giersch et al. | 512/8 |

FOREIGN PATENT DOCUMENTS 684880  4/1964  Canada ................. 568/821

*Primary Examiner*—Werren B. Lone
*Attorney, Agent, or Firm*—Sprung Horn Kramer & Woods

[57] ABSTRACT

The invention relates to new methylcyclododecatri-2,5,9-en-1-ols of formula

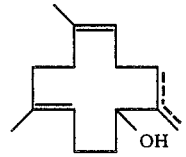

in which
one of the dashed lines represents a double bond and the other a single bond, and the endocyclic double bonds may be cis- and trans-configured, a process for their preparation and their use as scents.

3 Claims, No Drawings

METHYLCYCLODODECATRI-2,5,9-EN-1-OLS, A PROCESS FOR THEIR PREPARATION, AND THEIR USE

The invention relates to new methylcyclododecatri-2,5,9-en-1-ols, a process for their preparation, and their use as scents.

U.S. Pat. No. 3,723,478 disclosed the saturated alcohol 2,6,9-trimethyl-cyclododecan-1-ol as an intermediate for the preparation of the saturated ketone 2,6,9-trimethyl-cyclododecan-1-one; however, no reference was made to the sensory properties of the alcohol. U.S. Pat. No. 3,845,078 states that the mixture of the geometrical isomers of 1,5,9-trimethylcyclododeca-4,8-dien-1-ol has a tenacious, woody vetiver fragrance.

Surprisingly, it has now been found that methylcyclodedecatri-2,5,9-en-1-oles of the formula

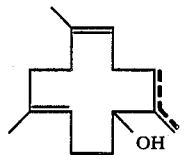

in which
one of the dashed lines represents a double bond and the other a single bond, and the endocyclic double bonds may be cis- and trans-configured,
in contrast to the known 2,6,9-trimethylcyclododecane derivatives, have a fine woody note suggestive of ambergris, musk and sandalwood and thus has extremely valuable scent properties which are desired in perfumery.

The invention therefore relates to methylcyclododecatri-2,5,9-en-1-oles of the formula I.

The compounds of the formula I according to the invention are 2,6,9-trimethyl-cyclododecatri-2,5,9-en-1-ol and its isomer 2-methylene-6,9-dimethylcyclododeca-2,5,9-en-1-ol.

The two compounds of the formula I are obtained by monoepoxidizing 1,5,10-trimethyl-cyclododeca-1,5,9-triene, a commercially available compound, in a fashion which is known per se using a peracid, and heating the monoepoxide obtained, 1,6,9-trimethyl-1,2-epoxycyclododeca-5,9-diene, in the presence of aluminium isopropylate. By heating the epoxidation product in the presence of aluminium isopropylate, an opening of the epoxy ring by isomerisation is achieved which proceeds virtually in one direction.

The invention therefore relates to a process for the preparation of the compounds of the formula I, characterized in that, 1,5,10-trimethylcyclododeca-1,5,9-triene is monoepoxidized in a fashion which is known per se, and the 1,6,9-trimethyl-1,2-epxoy-cyclododeca-5,9-diene obtained is isomerized by heating in the presence of aluminium isopropylate with opening of the epoxy group.

The epoxidization of the starting triene is carried out by the conventional processes which are described in the literature, for example in U.S. Pat. No. 3,723,478, using peracids such as perbenzoic acid, monoperphthalic acid, or preferably, peracetic acid in inert solvents such as chloroform, methylene chloride, benzene or, preferably, toluene. The small amounts of diepoxide which are produced at an approximately 10% excess of the peracid, relative to the cyclic triene, can easily be removed by distillation.

The isomerization of the monoepoxide can be carried out in the presence of inert solvents, for example toluene; however, the isomerization is preferably carried out without solvent. The aluminium isopropylate is used in an amount of 0.5 to 5 mol %, preferably 1 to 3 mol %, relative to the monoepoxide. The reaction is carried out at temperatures from 120° to 180° C., preferably 140° to 160° C., and preferably at, for example, a reduced pressure of 3 mbar to 7 mbar.

The invention furthermore relates to the use of the compounds of the formula I according to the invention as scents. They are used in combination with other scents which are known per se, as described, for example, in Arctander, Perfume and Flavor Chemicals, Montclair, N.J. (USA), 1969, and etherial oils, as described in Arctander, Perfume and Flavor Materials of natural Origin, Elisabeth, N.J. (USA), 1960. They give these fragrance compositions a subtle, long-lasting woody fragrance with well-rounded and fixing properties. In general, they are used in an amount of 1 to 80% by weight, preferably 3 to 25% by weight, relative to the fragrance composition.

The fragrance compositions produced using the compounds of the formula I according to the invention are highly suitable for perfuming finished products in the aerosol, washing agent and industrial chemistry sector, but in particular in the fine perfumery and cosmetics sector. The fragrance compositions and perfumed products are produced in a conventional fashion, for example by mixing the components.

EXAMPLE 1

1,938 g (10.2 mol) of peracetic acid (40% strength) are added over 2 hours with stirring to a mixture of 1,836 g (9 mol) of 1,5,10-trimethyl-cyclododeca-1,5,9-triene, 171 g (1.62 mol) of soda and 2,700 g of toluene at 10° to 20° C. The reaction mixture is stirred for 3 hours at 10° to 20° C. and subsequently diluted with 1,500 g of water. The organic phase is separated off, washed until neutral and freed from excess peroxide by adding iron-(II) ammonium sulphate. The solvent is then removed and the residue is distilled. The yield is 1,444 g (=72.9% of theory) of 1,6,9-trimethyl-1,2-epoxy-cyclododeca-5,9-diene, boiling point: 101° C./1 mbar.

1,444 g (6.55 mol) of the monepoxide thus obtained are heated to 140° to 145° C. after addition of 25 g (0.12 mol) of aluminium isopropylate, a vacuum of 5 mbar simultaneously being produced. After heating for 3 hours at the reflux temperature, the reaction mixture is subjected first to coarse distillation and then to fine distillation. 1,209 g (83.7% of theory) of the isomeric mixture of 2,6,9-trimethyl-cyclododecatri-2,5,9-en-1-ol and 2-methylene-6,9-dimethyl-cyclododecane-2,5,9-trien-1-ol, boiling point: 111° C./0.4 mbar, are obtained.

EXAMPLE 2

A perfume oil having a female note is produced by mixing the following components:

| | |
|---|---|
| Alpha-iso-methylionone | 100 |
| Phenylethyl alcohol | 70 |
| Hexenyl salicylate | 50 |
| Benzyl salicylate | 40 |
| Cyclopentadecanolide | 25 |
| Jasmine base | 50 |
| Rose base, de Mai type | 40 |

| | |
|---|---|
| Styrolyl acetate | 20 |
| Menthyl acetate | 80 |
| Acetanisole | 5 |
| Dimethylbenzylcarbinyl acetate | 40 |
| Methyl octinoate, 10% strength in dipropylene glycol | 5 |
| Alpha-hexylcinnamaldehyde | 60 |
| 4-(4-Hydroxy-4-methylpentyl)-3-cyclohexene-1-carboxaldehyde | 40 |
| Isoeugenol methyl ether | 80 |
| Musk ketone | 15 |
| 2-Tert.-butylcyclohexyl acetate | 30 |
| Allylamyl glycolate | 3 |
| Alpha-damascone | 2 |
| Nonadienal, 1% strength in diethyl phthalate | 6 |
| Ylang-ylang oil | 40 |
| Undec-8-en-1-al | 2 |
| 2,6,10-Trimethyl-2,5,9-cyclododecatrien-1-ol + isomer | 120 |
| Dipropylene gly | 77 |
| | 1,000 |

EXAMPLE 3

A perfume oil having a male note is produced by mixing the following components:

| | |
|---|---|
| Bergamot oil, African synthetic | 100 |
| Oil of rosemary | 20 |
| Lime oil, West-Indian distilled | 20 |
| Basil oil | 10 |
| Mugwort oil | 10 |
| Pine-needle oil | 20 |
| Allyl cyclohexylpropionate | 4 |
| Prenyl acetate | 1 |
| Hydroxycitronellal | 50 |
| Alpha-hexylcinnamaldehyde | 40 |
| 4-(4-Hydroxy-4-methylpentyl)-3-cyclohexene-1-carboxaldehyde | 30 |
| Dihydromyrcenol | 40 |
| Marjolia base | 50 |
| Oak moss, abs. Moroccan, 50% defatted | 30 |
| Patchouli oil, decolorized | 220 |
| 1,3,4,6,7,8-hexahydro-4,6,6,7,8,8-hexamethyl-cyclopenta-γ-2-benzopyran, 50% strength in diethyl phthalate | 100 |
| Methyl orcincarboxylate | 10 |
| 2,6,10-Trimethyl-2,5,9-cyclododecatrien-1-ol + isomer | 160 |
| Dipropylene glycol | 85 |
| | 1,000 |

What is claimed is:

1. A methylcyclododecatri-2,5,9-en-1-ol of the formula

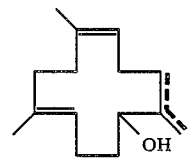

in which
one of the dashed lines is a double bond and the other is a single bond.

2. A process for the preparation of methylcyclododecatri-2,5,9-en-1-oles of the formula

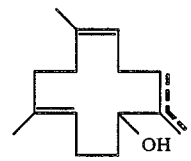

wherein
one of the dashed lines is a double bond and the other is a single bond,
which process comprises:
(a) monoepoxydising 1,5,10-trimethyl-cyclododeca-tri-1,5,9-ene with a peracid and
(b) isomerising the monoepoxide obtained, 1,6,9-trimethyl-1,2-epoxycyclododeca-5,9-diene, by heating in the presence of aluminum ispropylate.

3. A fragrance composition comprising an effective amount of a methylcyclododecatri-2,5,9-en-1-ol according to claim 1.

* * * * *

UNITED STATES PATENT AND TRADEMARK OFFICE
CERTIFICATE OF CORRECTION

PATENT NO. : 4,853,368

DATED : August 1, 1989

INVENTOR(S) : Neinhaus et al.

It is certified that error appears in the above-identified patent and that said Letters Patent is hereby corrected as shown below:

Col. 4, line 41   Delete " ispropylate " and substitute -- isopropylate --

Signed and Sealed this

Eighth Day of January, 1991

Attest:

HARRY F. MANBECK, JR.

*Attesting Officer*   *Commissioner of Patents and Trademarks*